United States Patent [19]

Spagnuolo et al.

[11] Patent Number: 5,039,691

[45] Date of Patent: Aug. 13, 1991

[54] 5-(1-(IMIDAZOL)METHYL)-3,3-DISUBSTITUTED-2(3H)FURANONE DERIVATIVES

[75] Inventors: Ciro J. Spagnuolo, Monmouth Junction, N.J.; Carl Kaiser, Millersville; Theodore Adams, Perry Hall, both of Md.

[73] Assignee: Marion Merrell Dow Inc., Kansas City, Mo.

[21] Appl. No.: 520,505

[22] Filed: May 8, 1990

Related U.S. Application Data

[63] Continuation-in-part of Ser. No. 362,932, Jun. 8, 1989, abandoned.

[51] Int. Cl.$^5$ ................. C07D 487/04; C07D 405/06; A61K 31/415
[52] U.S. Cl. .................................... 514/393; 514/210; 514/292; 514/300; 514/386; 514/387; 514/388; 514/389; 514/392; 514/397; 546/85; 546/121; 548/301; 548/302; 548/307; 548/309; 548/316; 548/323; 548/324; 548/336
[58] Field of Search ............... 548/324, 336, 323, 301, 548/302, 307, 309, 316; 514/393, 397, 210, 292, 300, 386, 387, 388, 389, 392; 546/121, 85

[56] References Cited

FOREIGN PATENT DOCUMENTS 2232132 6/1972 Fed. Rep. of Germany ...... 548/316
7005112 4/1969 Netherlands ........................ 546/121

*Primary Examiner*—Mary C. Lee
*Assistant Examiner*—Lenora Ava Miltenberger
*Attorney, Agent, or Firm*—Theresa M. Gillis

[57] ABSTRACT

Furanone compounds and compositions having anticholinergic activity are described. The compounds have the formula:

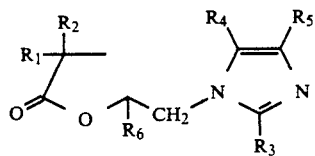

wherein:
the dashed line indicates either the 4,5-unsaturated or the 4,5-dihydrofuranone ring;
$R_1$ and $R_2$ may be the same or different and are hydrogen, thienyl, furanyl, or cycloalkyl ($C_3$-$C_6$), benzyl, phenyl, substituted phenyl or substituted benzyl wherein the phenyl or benzyl group may be substituted with halogen, trifluoromethyl, lower alkyl, lower alkoxy or hydroxy;
$R_3$, $R_4$ and $R_5$ may be the same or different and are hydrogen, lower alkyl, lower alkyl substituted with a halogen, alkoxy, amino or carboxylic acid group, an alkyl or alkylene bridge between $R_4$ and $R_5$ or $R_3$ and the ring N, trifluoromethyl, nitro, a cycloalkyl group containing 3 to 6 carbons, halogen, benzyl, phenyl, substituted phenyl or substituted benzyl, for which the substituents are the same as those set forth for $R_1$ and $R_2$ substituted benzyl or phenyl.

$R_6$ in the dihydrofuranone series is hydrogen or lower alkyl.

Also described are the pharmaceutically acceptable quaternary alkyl and acid addition salts of such compounds. The compounds are particularly useful in the treatment of neurogenic bladder disorder and chronic obstructive pulmonary diseases.

30 Claims, No Drawings

5-(1-(IMIDAZOL)METHYL)-3,3-DISUBSTITUTED-2(3H)FURANONE DERIVATIVES

This application is a continuation in part of application Ser. No. 07/362,932, filed June 8, 1989, now abandoned.

BACKGROUND OF THE INVENTION

A) Field of the Invention

This invention relates to novel 5-[1-(imidazol)methyl]-3,3-diphenyl-2(3H)furanone and 3-cycloalkyl-5-[1-(imidazol)methyl]-3-phenyl-2(3H)furanone derivatives, their pharmaceutically acceptable quaternary alkyl and acid addition salts and their use in disorders in which anticholinergic agents are effective.

B) State of the Art

Antagonism of the action of acetylcholine at muscarinic cholinergic receptors in various tissues produces antispasmodic, antisecretory and mydriatic effects. As a result, such compounds have a broad range of therapeutic applications, notably as antispasmodics, as an adjunct in the treatment of peptic ulcer, as adjuvants in the treatment of functional disorders of the bowel or bladder, such as irritable bowel syndrome, spastic colitis, ulcerative colitis, diverticulitis and neurogenic bladder disorders (B. V. Rama Sastry in "Burger's Medicinal Chemistry", M. E. Wolff, Ed., 4th Ed., Part III, chap. 44, pg. 361).

Furanones have long been known in the realm of natural products chemistry. Pilocarpine, a 4-[1-(imidazol)methyl]-2(3H)furanone is a naturally occurring muscarinic agonist (L. S. Goodman, A. Gilman, "The Pharmacological Basis of Therapeutics", 6th Ed., 1980, p. 87). 5-[(Diethylamino)-methyl]-4,5-dihydro-3,3-diphenyl-2(3H)furanone is a furanone for which antiarrhythmic effectiveness in mammalian heart tissue, but not anticholinergic properties, has been described (A. Pohland, S. African Patent 68 05,631, Mar. 2, 1970, Eli Lilly and Co., U.S. applied Nov. 13, 1967). Another furanone, a spasmolytic that prevents contractions of isolated guinea pig ileum, is 3-[(dimethylamino)methyl]-4,5-dihydro-5,5-diphenyl-2(3H)furanone (N. Kolokouris, G. Eytas, C. Brunet, M. Luyckx, Ann. Pharm. Fr., 43(3), 1985, p.257).

The majority of presently known antimuscarinic agents are structurally similar to solanaceous alkaloids, e.g., atropine, or a diverse group of compounds including hydroxyesters, e.g., oxybutynin, amides, e.g., tropicamide, and amino alcohols, e.g., procyclidine. These groups of compounds block the effect of acetylcholine on the cholinergic receptor. The isopropyl quaternary bromide of atropine, i.e. ipratropium bromide, is particularly noteworthy for its use as a bronchodilator in the treatment of respiratory disorders, such as asthma and chronic bronchitis (G. E. Pakes, R. N. Brogden, R. C. Heel, T. M. Speight, G. S. Avery, Drugs, 20, 1980, 237–266).

The present invention provides a novel class of 5-[1-(imidazol)methyl]-3,3-diphenyl-2(3H)furanone and 3-cycloalkyl-5-[1-(imidazol)methyl]-3-phenyl-2 (3H)furanone derivatives which have anticholinergic activity.

SUMMARY OF THE INVENTION

The invention provides novel compounds of the formula:

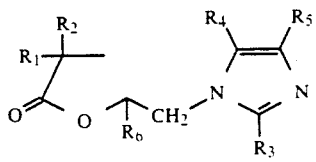

wherein:

the dashed line indicates either the 4,5-unsaturated or the 4,5-dihydrofuranone ring;

$R_1$ and $R_2$ may be the same or different and are hydrogen, thienyl, furanyl, or cycloalkyl ($C_3$–$C_6$), benzyl, phenyl, substituted phenyl or substituted benzyl wherein the phenyl or benzyl group may be substituted with halogen, trifluoromethyl, lower alkyl, lower alkoxy or hydroxy;

$R_3$ is hydrogen, lower alkyl, lower alkyl substituted with a halogen, alkoxy, amino, carboxylic acid, ester or amide group, benzyl, phenyl, nitro, trifluoromethyl, a cycloalkyl group containing 3 to 6 carbons, halogen, or part of an alkylene bridge to form a quaternary salt with the double bonded imidazole nitrogen, substituted phenyl or substituted benzyl, for which the substituents are the same as those set forth for $R_1$ and $R_2$ substituted benzyl or phenyl;

$R_4$ and $R_5$ may be the same or different and are the groups described for $R_3$ or are joined together to form an alkylene bridge;

$R_6$ is hydrogen or lower alkyl (in the 4,5-dihydrofuranone series); and the pharmaceutically acceptable salts of such compounds, particularly the quaternary alkyl ($C_1$–$C_4$) and acid addition salts of such compounds. (The foregoing formula is referred to herein as Formula I).

As used herein, lower alkyl or lower alkoxy refer to groups having one to six carbons and cycloalkyl ($C_3$–$C_6$) refers to cycloalkyls having three to six carbons in the cyclic group, including cyclopropyl, cyclobutyl, cyclopentyl or cyclohexyl. The alkylene bridges contemplated with respect to $R_3$, $R_4$ and $R_5$ may have one, two, three, four or more carbons. Each R group may be different than the other groups, i.e. each R group is independently selected. The invention includes lower alkyl quaternary salts of the foregoing compounds. The invention also includes pharmaceutical compositions effective as anticholinergics and therapeutic methods utilizing such compounds in those disorders in which anticholinergic agents are recognized to be effective, including treatment of neurogenic bladder disorders.

DETAILED DESCRIPTION OF THE INVENTION

The invention is directed to 5-[1-(imidazol)methyl]-3,3-diphenyl-2(3H)furanone and 3-cycloalkyl-5-[1-(imidazol)methyl]-3-phenyl-2(3H)furanone derivatives of Formula I set forth above. Compounds of the invention include those in which $R_1$ and $R_2$ are independently selected from phenyl, thienyl, furanyl and substituted phenyl and $R_3$, $R_4$ and $R_5$ are each independently a lower alkyl. Preferred compounds include those in which $R_1$ and $R_2$ are phenyl and $R_3$, $R_4$ and $R_5$ are each independently a lower alkyl. The preferred compounds of the invention are those in which $R_1$ and $R_2$ are phenyl or substituted phenyl. The most preferred $R_3$ groups are hydrogen and lower alkyl groups. Preferably R4 and R5 groups are both hydrogen or methyl. Among the preferred compounds are 5-[1-(2-ethylimidazol)methyl]-4,5-dihydro-3,3-diphenyl-2(3H)furanone, 5-[1-(2-propylimidazol)-methyl]-4,5-dihydro-3,3-diphenyl-2(3H)furanone, 5-[1-(2-methylimidazol)methyl]-4,5-dihydro-3,3-diphenyl-2(3H)furanone and 5-[1-(2-isopropylimidazol)methyl]-4,5-dihydro-3,3-diphenyl-2(3H)furanone. Other preferred compounds include (R)-(+)-5-[1-(2-ethylimidazol)methyl]-4,5-dihydro-3,3-diphenyl-2(3H)furanone, 5-[1-(2-n-propylimidazol)methyl]-4,5-dihydro-3,3-diphenyl-2(3H)furanone, 5-[1-(2-ethylimidazol)methyl]-3,3-diphenyl-2(3H)furanone, 5-[1-(2-ethyl-3-methylimidazol)methyl]-4,5-dihydro-3,3-diphenyl-2(3H)furanone bromide, 5-[1-(2-tert-butylimidazol)methyl]-4,5-dihydro-3,3-diphenyl-2(3H)furanone, 6,7-dihydro-1-[(2,3,4,5-tetrahydro-5-oxo-4,4-diphenyl-2-furanyl)methyl]-5H-pyrrolo[1,2-a]imidazolium chloride, 5-[1-(2-isopropylimidazol)methyl]-3,3-diphenyl-2(3H)furanone, (R)-(+)-5-[1-(2-isopropylimidazol)methyl]-4,5-dihydro-3,3-diphenyl-2(3H)furanone.

The compounds of the invention act as cholinergic receptor antagonists and have a variety of antimuscarinic therapeutic applications, particularly in the treatment of neurogenic bladder and pulmonary disorders. As a result of their action on bladder contraction, and their antispasmodic and antisecretory effects, they are of particular benefit in the treatment of urinary incontinence. The compounds also can be expected to produce antispasmodic, antisecretory and mydriatic effects useful in other disorders, notably as antispasmodics, as an adjunct in the treatment of peptic ulcer, and as adjuvants in the treatment of functional disorders of the bowel or bladder, such as irritable bowel syndrome, spastic colitis, ulcerative colitis and diverticulitis. The quaternary salts of this invention are particularly useful as bronchodilators, notably in the treatment of asthma and chronic bronchitis.

To the extent the compounds of the invention may exist as optical or geometric isomers, all isomers and racemic mixtures are to be understood to be included in the invention. In addition, all possible other isomeric forms of the compounds of the invention are within the ambit of this invention.

The compounds of this invention may be used in the form of a nontoxic, pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bismethylenesalicyclic, methanesulfonic, ethanedisulfonic, acetic, oxalic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

The compounds of this invention may be administered orally, parenterally, or by inhalation in conventional dosage unit forms such as tablets, capsules, injectables, aerosols, or the like, by incorporating the appropriate dose of a compound of Formula I with carriers according to accepted pharmaceutical practices.

Preferably a compound or an acid addition salt thereof is administered orally to an animal organism in a tablet, capsule or aerosol containing an amount sufficient to produce the desired activity of a cholinergic antagonist. Each dosage unit will contain the active ingredient in an amount of about 0.1 mg to about 40 mg. Advantageously equal doses will be administered three to four times daily with the daily dosage regimen being about 1 mg to about 160 mg, preferably from about 6 mg to about 80 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glycerol monostearate or glycerol distearate alone or with a wax.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be about 25 mg to about 1 g. If a liquid carrier is used, the preparation will be in the form of a syrup, emulsion, soft gelatin capsule, aerosol, sterile injectable liquid such as an ampoule, or an aqueous or non-aqueous liquid suspension.

The compounds of the invention can be prepared by alkylation of substituted acetic acids. For example, diphenylacetic acid was dilithiated and treated with allyl bromide to yield 2,2-diphenyl-4-pentenoic acid. This acid was cyclized to the furanone by treatment of its sodium salt with bromine. The resulting 5-(bromomethyl)-4,5-dihydro-3,3-diphenyl-2(3H)furanone is allowed to react with the substituted imidazole, under thermal conditions, to eventually give the compounds of the invention. Alternatively, a 2,2-disubstituted-4-pentenoic acid was oxidized to an epoxide which was treated with base to give a 5-hydroxymethyl-4,5-dihydro-3,3-disubstituted-2-(3H)furanone which was sequentially converted to the corresponding 5-bromomethyl or triflate derivative. This, in turn, was employed for alkylation of the appropriate imidazole, prepared from an alkyl cyanide via an imidate and condensation with aminoacetaldehyde dimethyl acetal, to produce a 5-[1-(imidazol)methyl]-4,5-dihydro-3,3-disubstituted-2(3H)furanone. Stereoselective syntheses of compounds of this invention proceeded from (R) and (S)-2,2-dimethyl-4-(hydroxymethyl)-1,3-dioxolane via the corresponding 4-iodomethyl derivative with which a phenylacetic acid was alkylated. Hydrolysis of the dioxolane afforded a diol, which following lactonization to the corresponding 5-hydroxymethyl-4,5-dihydro-3,3-disubstituted-2(3H)furanone, was used to alkylate an imidazole as indicated in preceding route. Base-induced dehydrohalogenation of 5-bromomethyl-4,5-dihydro-3,3-disubstituted-2(3H)furanones afforded 4,5-dehydro-5-methyl derivatives which, following bromination, were utilized to alkylate an appropriate imidazole to give the unsaturated (4,5-dehydro) 2-(3H)furanones of this invention. Quaternary alkyl derivatives were obtained by treatment of 5-[1-(imidazol)methyl]-3,3-disubstituted-2(3H) furanones with an alkyl halide or by appropriate alkylation of a quaternary alkylimidazole.

The following examples are illustrative of the invention. Temperature is expressed in degrees Celsius; NMR signals are given as ppm downfield from an internal standard of Me4Si.

EXAMPLES

EXAMPLE I

1-DIMETHYLAMINOMETHYLIMIDAZOLE

Imidazole (20.4 g, 0.3 mole) and 26 g (0.3 mole) of dimethylamine hydrochloride were stirred with 50 mL of water and the cooled solution adjusted to pH 4.97 with concentrated hydrochloric acid. A 37% solution of formaldehyde (27 g, 0.33 mole) was added and the mixture allowed to stand three days. The pH was adjusted to 14 with 20% aqueous potassium hydroxide before the product was salted out by adding solid $K_2CO_3$. The organics were extracted with methylene chloride, dried ($K_2CO_3$) and evaporated at reduced pressure. The residue was distilled in a Kugelrohr apparatus at 0.1 mm and 95° C. and gave 30.8 g (83%) of pure product.

2-BUTYLIMIDAZOLE

1-Dimethylaminomethylimidazole (5.0 g, 40 mmol.) was stirred in 80 mL of tetrahydrofuran under argon at −78° C. and 20 mL (48 mmol.) of 2.4 M n-butyllithium in hexane was added dropwise. After 1 hour, 8.8 g (48 mmol.) of 1-iodobutane was added and the mixture was stirred 1 hour at −78° C. before removing the cooling bath and stirring overnight. The reaction was made acidic by adding 60 mL of 2N hydrochloric acid and the organic solvents were evaporated at reduced pressure. Solid $NaHCO_3$ was added to the aqueous residue before extracting the mixture with methylene chloride. The extracts were dried ($MgSO_4$) and evaporated at reduced pressure to give an oil. Kugelrohr distillation at 0.1 mm and 125°–120° C., gave 2.1 g (43%) of product.

The following imidazoles were prepared by an analogous method.

2-Isobutylimidazole (mp 125°–126° C.),
2-Benzylimidazole (mp 123°–124.5° C.).

EXAMPLE II

2-TERT-BUTYLIMIDAZOLE tert-Butylnitrile (25 g, 0.3 mole) and 17.4 mL (0.3 mole) of absolute ethanol were stirred at 25° C. under argon and gaseous hydrogen chloride was slowly bubbled in the solution. After 5 days at 25° C., 200 mL of ether was added to afford 18.6 g (37%) of a solid which was characterized as ethyl tert-butylimidate. This product (18.6 g, 0.112 mole) was stirred in 20 mL of methanol and, after adding 13.0 g (0.123 mole) of aminoacetaldehyde dimethylacetal, the mixture was allowed to stand at 25° C. for 3 days. Concentration of the solution in vacuo at 88° C. gave 26.6 g of a residual liquid to which were added 30 mL of concentrated hydrochloric acid and 20 mL of water. The mixture was concentrated in vacuo at 88° C. to give 20 g of a dark viscous liquid. A suspension of this residue in 10 mL of water was adjusted to pH 10 with solid $K_2CO_3$. Following removal of the water in vacuo, the residue was stirred with 200 mL of ethanol. The resulting mixture was filtered and the filtrate was concentrated under reduced pressure to afford a solid residue. Sublimation of this solid afforded 9.0 g of a crystalline product, mp 224°–225° C.

The following imidazoles were prepared in an analogous manner:

2-Isobutylimidazole (mp 125°–126.5° C.),
2-Benzylimidazole (mp 123°–124° C.),
2-(2-Methoxyethyl)imidazole (Kugelrohr bp 90°–95° C. at 0.1 mm),
2-(2-Hydroxyethyl)imidazole (mp 128°–129° C.),
2-(4-Chlorobutyl)imidazole (an oil from chromotography and identified by $^1H$ NMR),
2-(3-Chloropropyl)imidazole (hygroscopic solid employed for further reaction without purification).

EXAMPLE III 5,6,7,8-TETRAHYDROIMIDAZO[1,2-A]PYRIDINE

To a solution of 11.0 g (69.3 mmol.) of 2-(4-chlorobutyl)imidazole in 90 mL of methyl ethyl ketone and 10 mL of dioxane was added 12.0 g (80.0 mmol.) of sodium iodide and 5.0 g (36.2 mmol.) of potassium carbonate. After the mixture was stirred and refluxed for 20 hours, it was cooled to 25° C. and filtered. The filtrate was concentrated in vacuo. The residue was dissolved in 40 mL of methanol, 10 mL of propylene oxide was added, and the solution was stirred at 25° C. for 20 hours. Concentration of the solution in vacuo afforded a liquid which was applied to 300 g of silica and eluted with 2% methanol in methylene chloride to give 2.2 g of a colorless liquid which was identified by $^1H$ NMR.

6,7-Dihydro-5H-pyrrolo[1,2-a]imidazole was prepared from 2-(3-chloropropyl)imidazole in a similar manner; it was sublimed at 80° C. and 0.1 Torr. to give a hygroscopic white solid.

EXAMPLE IV

8-METHYLIMIDAZO[1,2-A]PYRIDINE

To a mixture of chloroacetaldehyde [25.4 mL (0.2 mole) of a 50% aqueous solution] and 18.8 g (0.2 mole) of 2-amino-3-methylpyridine in 150 mL of water was added 16.8 g (0.2 mole) of sodium bicarbonate. After being stirred at 25° C. for 3 days, the mixture was acidified with concentrated hydrochloric acid and stirred an additional 30 minutes. After the pH was adjusted to 10 by addition of sodium hydroxide, the mixture was saturated with sodium chloride and extracted with ether. The ether extracts were dried and concentrated to give 16.3 g (62%) of a liquid residue, bp 68°–70° C. at 0.1 Torr.

Imidazo[1,2-a]pyridine, bp 61°–66° C. at 0.1 Torr., was prepared in an analogous manner.

EXAMPLE V 5,6,7,8-TETRAHYDRO-8-METHYLIMIDAZO[1,2-A]PYRIDINE

A mixture of 2.0 g (15.1 mmol.) of 8-methylimidazo[1,2-a]pyridine and 2 teaspoonsful of Raney nickel 2800 in 40 mL of n-butanol was hydrogenated at an initial pressure of 55 psi of hydrogen at 65° C. for 24 hours. The mixture was filtered and the filtrate was concentrated in vacuo. The residual liquid was chromatographed (silica, 40 g, 98: 2; methylene chloride: methanol to give 1.1 g of product as an oil. $^1H$ NMR($CDCl_3$)δ 1.32(d, J=7.4 Hz, 3H), 1.42–1.58(m 1H), 1.82–2.0(m, 1H), 2.0–2.12(m, 2H), 2.82–2.99(m, 1H) 3.80–4.02(m, 2H), 6.74(d, J=1.5 Hz, 1H), 6.97(d, J=1.5 Hz, 1H); analytical TLC (silica, 95: 5, methylene chloride: methanol) Rf 0.46.

EXAMPLE VI

2-ETHYL-1-METHYLIMIDAZOLE

A mixture of 50 g (0.52 mole) of 2-ethylimidazole, 104 g (0.78 mole) of potassium carbonate, 1.4 g (5.2 mmol.) of [18]-crown 6 and 260 mL of dimethyl carbonate was stirred and refluxed for 3 days. The mixture was then filtered and the filter cake was washed with ether. The filtrate and washings were concentrated in vacuo and the resulting residue was partitioned between water and ether. After the ether layer was separated, it was dried over $MgSO_4$, concentrated and distilled to give 17 g (30%) of a colorless liquid, bp 65–75° C. at 0.1 Torr.

2-Isopropyl-1-methylimidazole, a colorless liquid, bp 70° C. at 0.1 Torr, was prepared in an analogous manner.

EXAMPLE VII

1-TRITYLIMIDAZOLE

To a stirred solution of 23.5 g (0.35 mole) of imidazole in 425 mL of ethyl acetate was added 48.0 g (0.32 mole) of triphenylmethyl chloride. The mixture was stirred for 20 hours and then 500 mL of water was added. After being stirred for an additional 2 hours, the mixture was filtered. The ethyl acetate layer was separated, dried ($MgSO_4$) and concentrated. Recrystallization of the residue from xylene gave 41 g of white crystals, mp 222°–225° C..

2-CARBOMETHOXY-1-TRITYLIMIDAZOLE

To a stirred solution of 12.4 g (40 mmol.) of 1-tritylimidazole in 250 mL of tetrahydrofuran, under argon, at 0° C. was added 20 mL (48 mmol.) of a solution of n-butyl-lithium in hexane. After the solution was allowed to warm to ambient temperature, it was stirred for 1 hour and then 3.4 mL (50 mmol.) of methyl chloroformate was added dropwise. The mixture was stirred for 20 hours at 25° C., 100 mL of water was added and then the mixture was concentrated in vacuo. The residue was extracted with ether. After the extracts were dried ($MgSO_4$) and concentrated, the residue was chromatographed on 200 g of silica using 1:3 ethyl acetate: hexane, followed by 1:1 ethyl acetate: hexane, and finally ethyl acetate to give 3.2 g of colorless product.

2-CARBOMETHOXYIMIDAZOLE

After a solution of 3.2 g (8.7 mmol.) of 1-trityl-2-carbomethoxyimidazole in 40 mL of a 5% solution of acetic acid in methanol was refluxed for 30 minutes, it was concentrated in vacuo. Recrystallization from ethanol afforded colorless needles, mp 187°–188° C.

EXAMPLE VIII

2,2-DIPHENYL-4-PENTENOIC ACID

A solution of diphenylacetic acid (250 g., 1.17 mol ) in 2.4 L of tetrahydrofuran was stirred at 0° C. under argon while 0.94 L of a 2.5M solution on n-butyllithium in hexane was added dropwise. After 1 hour, allyl bromide (142.5 g, 1.17 mole) was added in one portion. After 15 minutes, 500 mL of 10% hydrochloric acid was added, along with ether (2 L). The layers were separated, the aqueous layer extracted with ethyl ether (1×250 mL), the organic layers combined, washed with brine, dried ($MgSO_4$), and filtered. Concentration afforded 296 g (99%) of an off-white solid, mp 134°–137° C. 1H NMR ($CDCl_3$) δ 7.3 (m, 10H), 5.6 (m, 1H), 4.9 (bs, 2H), 3.2 (d, 2H).

5-BROMOMETHYL-4,5-DIHYDRO-3,3-DIPHENYL-2(3H)FURANONE

To a stirred mixture of tetrahydrofuran:water (9:1, 1.65 L) was added 2,2-diphenyl-4-pentenoic acid (296 g, 1.17 mole) and sodium bicarbonate (98.85 g, 1.17 mole). After the mixture had become homogeneous, bromine (188 g, 1.17 mole) was added dropwise. After 1 hour, a solution of sodium thiosulfate (10 g) in 250 mL of water was added, then the mixture was stirred for 10 minutes. Ether (1 L) was added and the layers separated. The organic layer was washed with brine, dried ($MgSO_4$), and filtered. Concentration afforded 364 g of an oil which crystallized upon standing. Recrystallization from ether gave 230 g (59%) of a white crystalline solid, mp 84°–85° C. IR (KBr) 1766 $cm^{-1}$. $^1H$ NMR ($CDCl_3$) 7.45–7.27 (m, 10H), 4.5 (m, 1H), 3.5 (m, 2H), 3.2 (dd, 1H, J=13.1), 2.8 (dd, 1H, J=10, 13 1).

5-[1-(IMIDAZOL)METHYL]-4,5-DIHYDRO-3,3-DIPHENYL-2(3H)FURANONE 5-(Bromomethyl)-4,5-dihydro-3,3-diphenyl-2(3H)furanone (1.5 g, 4.5 mmol.) and imidazole (2 g) were dissolved in dimethylformamide (6 mL). This solution was heated under argon to 100° C. for 20 hours. After being cooled, the mixture was partitioned between saturated sodium bicarbonate solution (25 mL) and methylene chloride (200 mL) and the layers separated. The organic layer was washed with water (2×50 mL), then washed with brine and dried ($MgSO_4$). Filtration, followed by concentration, afforded a solid. Recrystallization from ether gave (0.7 g, 50%) of a white solid, mp 146°–148° C. IR (KBr) 1777 $cm^{-1}$. $^1H$ NMR ($CDCl_3$) 7.5–7.1 (m, 13H), 4.55 (m, 1H), 4.3 (dd, 1H), 4.16 (dd, 1H), 2.99 (dd, 1H), 2.5 (dd, 1H). Anal. calcd. for $C_{20}H_{18}N_2O_2$: C, 75.45; H, 5.69; N, 8.79. Found: C, 75.31; H, 5.76; N, 8.71.

EXAMPLE IX

5-[1-(3-METHYLIMIDAZOL)METHYL]-4,5-DIHYDRO-3,3-DIPHENYL-2(3h)FURANONE BROMIDE HYDRATE 5-(Bromomethyl)-4,5-dihydro-3,3-diphenyl-2(3H)furanone (1.35 g, 4.07 mmol.), 1-methylimidazole (0.35 g, 4.07 mmol.) and ether (5 mL) were placed into a sealed tube. The tube was filled with argon, capped and heated at 110° C. for 18 hours. After the solution was cooled, the gummy residue was removed and triturated with acetone to give a crystalline solid. Recrystallization from acetone afforded a white, hydroscopic solid, mp 148°–152° C. (0.70 g, 42%). IR (KBr) 1758 $cm^{-1}$. $^1H$ NMR (DMSO-$d_6$) 9.1 (S, 1H), 7.7 (dd, 2H), 7.4–7.4 (m, 10H), 4.6 (m, 1H), 3.86 (S, 3H), 3.3 (dd, 1H), 2.8 (dd, 1H). Anal. calcd. for $C_{21}H_{21}N_2O_2Br \cdot H_2O$: C, 58.47; H, 5.37; N, 6.49; Br, 18.52. Found: C, 57.91; H, 5.40; N, 6.40; Br, 18.41.

The following compounds (melting point in parentheses) were also prepared by the sequence of reactions set forth in Examples VIII and IX.

5-[(1-Imidazol)methyl]-4,5-dihydro-3,3-diphenyl-2(3H)furanone (146°–148° C.),

5-[1-(2-Methylimidazol)methyl]-4,5-dihydro-3,3-diphenyl-2(3H)furanone (106°–108° C.), 5-[1-(2-Ethylimidazol)methyl]-4,5-dihydro-3,3-diphenyl-2(3H) furanone hydrochloride (265°–268° C.), 5-[1-(3-Methylimidazol)methyl]-4,50-dihydro-3,3-diphenyl-2(3H)furanone bromide hydrate (148°-152° C.),
5-[1-(2,3-Dimethylimidazol)methyl]-4,5-dihydro-3,3-diphenyl-2(3H)furanone bromide (240°-243° C.),
5-[1-(2-Methyl-3-benzylimidazol)methyl]-4,5-dihydro-3,3-diphenyl-2(3H)furanone bromide (218°-220° C.),
5-[1-(2-Isopropylimidazol)methyl]-4,5-dihydro-3,3-diphenyl-2(3H)furanone (108°-109° C.),
5-[1-(2-Butylimidazol)methyl]-4,5-dihydro-3,3-diphenyl-2(3H)furanone (134°-135° C.),
5-[1-(Propylimidazol)methyl]-4,5-dihydro-3,3-diphenyl-2(3H)furanone (168°-169° C.),
5-[1-(3-Ethylimidazol)methyl]-4,5-dihydro-3,3-diphenyl-2(3H)furanone (155°-160° C.).

EXAMPLE X

5-(HYDROXYMETHYL)-4,5-DIHYDRO-3,3-DIPHENYL-2(3H)-FURANONE 2,2-Diphenyl-4-pentenoic acid (5.0 g, 20 mmol.), 20 mL of formic acid and 2.4 mL (22 mmol.) of 30% hydrogen peroxide were stirred at 70° C. for 25 hours at ambient temperature. The solvents were evaporated at reduced pressure, the residue taken up in 20 mL of methanol and a solution of 750 mg solid NaOH in 10 mL of water was added. The mixture was warmed at 70° C. to solution, about 1 hour before cooling and acidifying with 6N hydrochloric acid. The product was extracted with ether, the organics dried (MgSO$_4$) and evaporated at reduced pressure to give an oil in quantitative yield, the H NMR indicated a clean reaction product which was carried on without further purification. Analytical TLC (silica, 9:1, methylene chloride: EtAc) R$f$ 0.35; IR (neat) 3419, 3060, 2936, 1763, 1177, 786, 763, 699 cm$^{-1}$; $^1$H NMR (CDCl$_3$)δ 2.5-2.65 (bs, 1H), 2.84-3.02 (m, 2H), 3.64-3.72 (m, 1H), 3.92-4.00 (m, 1H), 4.41-4.51 (m, 1H), 7.2-7.4 (m, 10H).

5-(TRIFLUOROMETHANESULFONYLOXYMETHYL)-4,5-DIHYDRO-3,3-DIPHENYL-2(3H)FURANONE

Trifluoromethanesulfonic anhydride, 5.5 mL (32.5 mmol.), was added to 14 mL dry methylene chloride under argon at room temperature. The solution was cooled to −40° C. and 2.3 g (22 mmol.) of finely powdered, oven dried Na$_2$CO$_3$ was added. To the stirred mixture 6.7 g (25 mmol.) of 5-(hydroxymethyl)-4,5-dihydro-3,3-diphenyl-2(3H)furanone in 15 mL of methylene chloride was added dropwise, stirring 2 hours at −40° C. before warming to 0° C. for 0.5 hours. The reaction was quenched at 0° C. by adding 10 mL of water dropwise with vigorous stirring. The layers were separated, the organics washed with brine, dried (MgSO$_4$), and evaporated at reduced pressure to a solid. This material was used as received and usually contained 5 to 15% of unreacted alcohol. 1H NMR (CDCl$_3$)δ 2.77-2.83 (m, 1H), 3.05-3.14 (m, 1H), 4.51-4.71 (m, 2H), 4.7-4.75 (m, 1H), 7.25-7.45 (m, 10H).

5-[1-(2-N-PROPYLIMIDAZOL)METHYL]-4,5-DIHYDRO-3,3-DIPHENYL-2(3h)-FURANONE HYDROCHLORIDE

5-Trifluoromethanesulfonyloxymethyl-4,5-dihydro-3,3-diphenyl-2(3H)furanone (5.2 g, 13 mmol.) and 3.0 g (28 mmol.) of 2-n-propylimidazole were stirred in 15 mL of methylene chloride under argon in a sealed tube and heated at 120° C. overnight. After the cooled solution was poured onto water, the organics were washed with dilute aqueous K$_2$CO$_3$, brine, and dried (MgSO$_4$) before evaporation at reduced pressure to give an oil. The resuide was chromatographed (silica, 98: 2, methylene chloride: methanol) to give 3.0 g (64%) of product. This material was dissolved in warm isopropanol, 1 equivalent of 1N hydrochloric acid in ether was added, and the product allowed to crystallize, mp 232°-234° C. $^1$H NMR(DMSO-d$_6$)δ .905(t, J=7.4 Hz, 3H), 1.63-1.79(m, 2H), 2.79-2.89(m, 1H), 2.95(t, J=7.5 Hz 2H), 3.23-3.33(m, 1H), 4.48-4.70(m, 3H), 7.23-7.43(m, 10H), 7.61(d, J=1.8 Hz, 1H), 7.66(d, J=1.8 Hz, 1H); IR(KBr) 3062, 2957, 2933, 2872, 1761, 1493, 1445, 1277, 1169, 1069, 696 cm$^{-1}$; analytical tlc (silica, 95: 5, methylene chloride: MeOH) R$f$ .39. Anal. calcd. for C$_{23}$H$_{25}$ClN$_2$O$_2$: C, 69.60; H, 6.35; Cl, 8.93; N, 7.06. Found: C, 69.62; H, 6.37; Cl, 8.97; N, 7.04.

The following compounds were prepared in an analogous manner.

5-[1-(2-Isopropylimidazol)methyl]-4,5-dihydro-3,3-diphenyl-2(3H)furanone hydrochloride (mp 250.5°-252.5° C.), 5-[1-(2-Isobutylimidazolmethyl]-4,5-dihydro-3,3-diphenyl-2(3H)furanone, hydrochloride (mp 223°-27° C.), 5-[1-(2-tert-Butylimidazol)methyl]-4,5-dihydro-3,3-diphenyl-2(3H)furanone hydrochloride hydrate (mp 118°-130° C.), 5-[1-(2-Phenylimidazol)methyl]-4,5-dihydro-3,3-diphenyl-2(3H)furanone hydrochloride (mp 189°-190.5° C.), 5-{1-[2-(2-methoxyethyl)imidazol]methyl}-4,5-dihydro-3,3-diphenyl-2(3H)furanone hydrochloride (mp 236°-237° C.).

EXAMPLE XI

5-[1-(2-ETHYL-3-METHYLIMIDAZOL)METHYL]-4,5-DIHYDRO-3,3-DIPHENYL2(3H)FURANONE CHLORIDE HYDRATE

1-Methyl-2-ethylimidazole (2.5 g, 22 mmol.) and 8.0 g (20 mmol.) of 5-trifluoromethanesulfonyloxymethyl-4,5-dihydro-3,3-diphenyl-2(3H)furanone were mixed with 15 mL of methylene chloride under argon in a sealed tube and heated 1.2 hours at 100° C. Upon cooling, a solid formed and was filtered. The solvents were evaporated at reduced pressure and the residue and the solid were recrystallized from isopropanol to give 6.5 g (61%) of pure triflate salt. The solid was taken up in 180 mL of methanol and passed through 180 mL of Amberlite IRA-400(Cl). The resulting solid was recrystallized from acetone to give 4.8 g of product, mp 243°-245° C. $^1$H NMR(CDCl$_3$)δ 1.17(t, J=7.5 Hz, 3H), 2.81-2.91(m, 1H), 3.03-3.14(m, 2H), 3.26-3.34(m, 1H), 3.80(s, 3H), 7.21-7.43(m, 10H), 7.66(d, J=2.0 Hz, 1H), 7.71(d, J=2.0 Hz, 1H); IR(KBr) 3478, 3409, 3108, 3077, 1769, 1531, 1447, 1159, 1061, 964, 753, 704 cm$^{-1}$; analytical TLC (silica, 95: 5, methylene chloride: MeOH) R$f$.26. Anal. calcd. for C$_{23}$H$_{25}$ClN$_2$O$_2$.0.05 H$_2$O): C, 68.05; H, 6.46; N, 6.90; Cl, 8.73. Found: C, 68.24; H, 6.45; N, 7.10; Cl, 8.97.

5-[1-(2-Isopropyl-3-methylimidazol)methyl]-4,5-dihydro-3,3-diphenyl-2(3H)furanone chloride hydrate was prepared in an analogous manner, mp 156°-159° C.

EXAMPLE XII

5-[1-(2-CARBOMETHOXYIMIDAZOL)METHYL]-4,5-DIHYDRO-3,3-DIPHENYL-2(3H)FURANONE HYDROCHLORIDE

To a stirred solution of 0.11 g (0.87 mmol.) of 2-carbomethoxyimidazole in 5 mL of dimethylformamide, under argon, was added 34 mg (1.5 mmol.) of sodium hydride. The mixture was stirred until solution was completed (about 1 hour) and then 0.5 g (1.2 mmol.) of 5-(trifluoromethanesulfonyloxymethyl)-4,5-dihydro-3,3-diphenyl-2(3H)furanone was added. After being stirred for 20 hours, the solution was concentrated in vacuo. The residual semi-solid was partitioned between methylene chloride and water. The organic layer was separated, washed with water, dried over $MgSO_4$ and concentrated in vacuo. The residue was applied to a preparative TLC plate (silica, 2 mm × 20 cm × 20 cm) using methanol: methylene chloride (5:95). Elution of the major spot gave 300 mg (91%) of base. To a solution of this material in ethyl acetate was added an equivalent of 1N hydrogen chloride in ether to afford colorless crystals, mp. 151°-152° C. $^1$H NMR(CDCl$_3$)δ 2.62-2.76(m, 1H), 3.20-3.28(m, 2H), 4.07(s, 3H), 4.65-4.77(m, 2H), 5.14-5.23(m, 1H), 7.22-7.40(m, 10H), 7.56(s, 1H), 7.63(s, lH); IR(KBr) 3432, 2519, 1765, 1745, 1460, 1447, 1270, 1172, 960, 699 cm$^{-1}$; analytical TLC (silica, 96:4, methylene chloride: methanol) R$f$ 55. Anal. calcd. for $C_{22}H_{21}ClN_2O_4$: C, 64.00; H, 5.13; Cl, 8.59; N, 6.78. Found: C, 64.29; H, 5.24; Cl, 8.43; N, 6.56.

The following compounds were prepared in an analogous manner.

5-[(2-Nitroimidazol)methyl]-4,5-dihydro-3,3-diphenyl-2(3H)furanone Hydrochloride (mp 190°-205° C.), 5-[1-(2-Benzylimidazol)methyl]-4,5-dihydro-3,3-diphenyl-2(3H)furanone Hydrochloride (mp 256°-260° C.).

EXAMPLE XIII

6,7-DIHYDRO-1-[(2,3,4,5-TETRAHYDRO-5-OXO-4,4-DIPHENYL-2-FURANYL)METHYL-5H-PYRROLO[1,2-A] IMIDAZOLIUM CHLORIDE

A mixture of 2.0 g (18.5 mmol.) of 6,7-dihydro-5H-pyrrolo[1,2-a]imidazole and 5.0 g (12 5 mmol.) of 5-(trifluoromethylsulfonyloxymethyl)-4,5-dihydro-3,3-diphenyl-2(3H)furanone in 20 mL of methylene chloride under argon in a sealed tube was heated at 100° C. for 20 hours. After being cooled to 25° C., the reaction mixture was washed successively with brine and water, dried over $MgSO_4$ and concentrated. The residual liquid was chromatographed on 135 g of silica eluting with 98:2 and then 96:4 methylene chloride: methanol to give 4.0 g (63%) of product. This triflate salt in 60 mL of methanol was passed through a column of 150 mL of Amberlite IRA-400 (Cl anion exchange resin). Concentration of the eluate afforded 2.6 g of colorless crystals, mp 245°-246° C. $^1$H NMR(CDCl$_3$)δ 2.67(dd, J=10.3 Hz, J=13.4 Hz, 1H), 2.78-2.91(m, 2H), 3.42-3.66(m, 3H), 4.24-4.36(m, 2H), 4.37-4.48(m, 1H), 4.82-4.93(m, 1H), 5.41(dd, J=1.7 Hz, J=14.6 Hz, 1H), 7.21-7.43(m, 1H), 8.21(d, J=1.8 Hz, 1H); IR(KBr) 3484, 3399, 3093, 3062, 1764, 1553, 1447, 1164, 964, 709 cm$^{-1}$; analytical TLC (silica, 9: 1, methylene chloride: MeOH) R$f$ 0.14. Anal. calcd. for $C_{23}H_{23}ClN_2O_2 + 0.75 H_2O$: C, 67.64; H, 6.05; N, 6.86; Cl, 8.68. Found: C, 67.71; H, 6.06; N, 6.92; Cl, 8.69.

The following compounds were prepared in an analogous manner.

5,6,7,8-Tetrahydro-1-[(2,3,4,5-tetrahydro-5-oxo-4,4,-diphenyl-2-furanyl)methyl]imidazo[1,2-a]pyridinium chloride hydrate (mp 235.5°-237° C.), 5,6,7,8-Tetrahydro-8-methyl-1-[2,3,4,5-tetrahydro-5-oxo-4,4-diphenyl-2-furanyl)methyl]imidazo[1,2-a]pyridinium chloride (mp 220°-225° C.), 1-[(2,3,4,5-Tetrahydro-5-oxo-4,4-diphenyl-2-furanyl)-methyl]-8-methylimidazo[1,2-a]pyridinium chloride hydrate (mp 232.5-234.5° C.), 1-[(2,3,4,5-Tetrahydro-5-oxo-4,4-diphenyl-2-furanyl)-methyl]imidazo[1,2-a]pyridinium chloride hydrate (mp 266°-268° C.).

EXAMPLE XIV

(S)-(+)-2,2-DIMETHYL-1,3-DIOXOLAN-4-METHYL P-TOLUENESULFONATE

To a stirred solution of 490 g (2.57 mole) of p-toluenesulfonyl chloride in 2 L of methylene chloride was added dropwise 391 mL (2.81 mole) of triethylamine. The stirred solution was cooled to 0° C. and 338.2 g (2.56 mole) of (R)-glycerol acetonide was added dropwise. The reaction mixture was stirred at 0° C. for 2 hours and at 25° C. for 20 hours. After the mixture was filtered, the filtrate was washed successively with 1N hydrochloric acid, water and a saturated solution of sodium bicarbonate. The methylene chloride solution was then dried over $MgSO_4$ and concentrated to give 610 g (83%) of a pale yellow liquid. GC analysis on PH5-crosslinked 5% toluene silicone 25 m×0.2 mm×0.11 mm film thickness, Ti 100° C. 3 min, then 15°/min to 300° C., Tr 11.83 min (100%). Optical rotation for 0.171 g diluted to 1.0 mL in 95% ethanol at 22° C. [α]D +4.11°. IR (neat) 2992, 1594, 1365, 1182, 1090, 977, 825 cm$^{-1}$. $^1$H NMR(CDCl$_3$)δ 7.79 (d, 2H), 7.35 (d, 2H), 4.27 (m, 1H), 4.06-3.97 (m, 3H), 3.78-3.73 (m, lH), 2.45 (s, 3H), 1.31 (s, 3H). Anal. calcd. for $C_{13}H_{18}O_5S$: C, 54.53; H, 6.34; S, 11.20 Found: C, 54.51; H, 6.35; S, 11.14.

(S)-(−)-2,2-DIMETHYL-4-IODOMETHYL-1,3-DIOXOLANE

To a solution of 9.6 g (33.4 mmol.) of (S)-(+)-2,2-dimethyl-1,3-dioxolan-4-methyl p-toluenesulfonate in 20 mL of dimethylformamide was added in portions at 45° C., 5.0 g 33.4 mmol.) of sodium iodide. The reaction mixture was stirred at 78° C. for 20 hours. After being cooled to 25° C., the mixture was filtered. To the filtrate was added 200 mL of water and 250 mL of ether. The ether layer was separated, washed successively with 1N hydrochloric acid, water, aqueous sodium bicarbonate and brine. After the solution was dried over $MgSO_4$, it was concentrated to afford 2.9 g (83%) of an orange-red liquid. TLC (silica, ethyl acetate: hexane, 1:9) R$f$ 0.38. GC analysis on PH5-crosslinked 5% toluene silicone 25 m×0.2 mm×0.11 mm film thickness, Ti 100° C. 3 min, then 15./min to 300° C., Tr 4.13 min (100%). Optical rotation for 0.036 g of iodide diluted to 2.0 mL in 95% ethanol at 22° C. [α]D −27.0°. IR (neat) 2987, 2869, 1450, 1378, 1252, 1218, 1149, 1059, 845 cm$^{-1}$. $^1$H NMR(CDCl$_3$)δ 4.35-4.23 (m, 1H), 4.17-4.12 (m, 1H), 3.81-3.76 (m, 1H), 3.28-3.23 (m, 1H), 3.17-3.11 (m, 1H), 1.15 (s, 3H), 1.34 (s, 3H)

(R)-(+)-3-[(2,2-DIMETHYL-1,3-DIOXOLANYL)-METHYL]-2,2-DIPHENYLPROPIONIC ACID

To a solution of 39.2 g (0.185 mole) of diphenylacetic acid in 100 mL of tetrahydrofuran was added 309 mL (0.463 mole) of a 1.5 M solution of lithium diisopropylamide mono (tetrahydrofuran) in cyclohexane in 300 mL of tetrahydrofuran at 0° C. The resulting mixture was stirred at 25° C. for 30 minutes and then at 70° C. for 1 hour. After being cooled to 0° C., 67.1 g (0.227 mole) of (S)-(−)-2,2-dimethyl-4-iodomethyl-1,3-dioxolane was added dropwise and stirring was continued at 0° C. for 30 minutes and then at 25° C. for 20 hours. The reaction mixture was poured into 800 mL of ice-water and extracted with ethyl acetate. The aqueous part was acidified (pH 4) with 2.5N hydrochloric acid and saturated with sodium chloride. The mixture was extracted with ethyl acetate. After the organic extracts were washed with brine, they were dried (MgSO$_4$) and concentrated to give 44.5 g (74%) of a red oil. $^1$H NMR (CDCl$_3$)δ 7.38–7.25 (m), 3.95–3.85 (m, 1H), 3.30–3.15 (m, 1H), 2.95–2.90 (m, 1H), 2.35–2.30 (m, 1H), 1.23 (s, CH$_3$), 1.25 (s, CH$_3$).

(R)-(+)-5-HYDROXYMETHYL-4,5-DIHYDRO-3,3-DIPHENYL-2(3H)FURANONE

A solution of 44.5 g (0.136 mole) of (R)-(+)-3-[(2,2-dimethyl-1,3-dioxolanyl)methyl]-2,2-diphenylpropionic acid in 300 mL of methanol and 300 mL of water wa acidified (pH 1) with 6 N hydrochloric acid. After the reaction mixture was stirred at 25° C. for 2.5 hours, it was concentrated in vacuo. The residue was extracted into ether. The ether extracts were washed successively with 10% aqueous sodium bicarbonate and brine, dried (MgSO$_4$). and concentrated to afford 29.1 g (80%) of a yellow liquid. TLC (silica, ethyl acetate: methlene chloride, 1:9) R$f$ 0.40. Optical rotation for 0.038 g diluted to 2.0 mL with 95% ethanol at 23° C. [α]D+54.63°. IR (neat) 3420, 2972, 2860, 1746, 1498, 1448, 1177, 1110, 699, 675 cm$^{-1}$. $^1$H NMR (CDCl$_3$) δ 7.37–7.24 (m, 1H), 4.52–4.42 (m, 1H), 3.98 (dd, J=2.80 Hz, 1H), 3.69 (dd, J=4.56 Hz, 1H), 3.01–2.85 (m, J=4.13 Hz, J=2.88 Hz, 2H), 2.30 (br s, 1H).

(R)-(+)-5-TRIFLUOROMETHANESULFONYLOXYMETHYL-4,5-DIHYDRO-3,3-DIPHENYL-2(3H)FURANONE

To a solution of 50 g (0.177 mole) of trifluoromethanesulfonic acid anydride in 50 mL of methylene chloride under argon at −60° C. was added 10.1 g (0.095 mole) of sodium carbonate followed by dropwise addition of a solution of 29 g (0.11 mole) of (R)-(+)-5-hydroxymethyl-3,3 -diphenyl-4,5-dihydro-2(3H)furanone in 100 mL of methylene chloride. After being stirred for 2 hours at −60° C. and 1 hour at 0° C., 35 mL of water was added slowly. The organic layer was separated, washed with brine, dried (MgSO$_4$) and concentrated in vacuo to give 37.8 g (88%) of a liquid product. TLC (silica, hexane: ethyl acetate, 7:3) R$f$ 0.51. Optical rotation for 0.185 g of product diluted to 1.0 mL in chloroform at 23° C.: [α]D+48.64°. $^1$H NMR (CDCl$_3$)δ 7.39–7.24 (m, 10H), 4.71 (dd, J=2.19 Hz, 1H), 4.64–4.60 (m, 1H), 4.59–4.53 (m, 1H), 3.05 (dd, J=5.10 Hz, 1H), 2.81 (dd, J=10.14 Hz, 1H).

(R)-(+)5-[1-(2-ISOPROPYLIMIDAZOL)METHYL]-4,5-DIHYDRO-3,3-DIPHENYL-2(3H)FURANONE

To a mixture of 4.33 g (11 mmol.) of (R)-(+)-5 -trifluoromethanesulfonyloxymethyl-4,5-dihydro-3,3-diphenyl-2(3H)furanone in 30 mL of methylene dichloride was added 2.2 g (20 mmol.) of 2-isopropylimidazole. The mixture was placed under argon in a sealed tube and heated at 110° C. for 20 hours. After being cooled to 25° C., the mixture was washed with 5% aqueous potassium carbonate and brine. The methylene chloride solution was dried (MgSO$_4$) and concentrated in vacuo. The crude residue was purified by flash chromotagraphy (silica gel, 100 g, 40–60 mesh, methanol: dichloromethane, 2:98) to give 3.2 g (82%) of a slightly pale yellow foam. TLC (silica, methanol: dichloromethane, 1:9) R$f$ 0.76. Optical rotation for 0.0156 g diluted to 2.0 mL with 95% ethanol at 23° C. [α]D+36.15°. IR (KBr) 3400, 2975, 2918, 1760, 1495, 1447, 1275, 1170, 962, 699 cm$^{-1}$. $^1$H NMR (CDCl$_3$)δ 7.38–7.18 (m, 10H), 6.92 (d, J=1.2 Hz, 1H), 6.70 (d, J=1.2 Hz, 1H), 4.58–4.52 (m, 1H), 4.28–4.12 (m, 2H), 3.06–2.92 (m, 2H), 2.65–2.54 (m, 2H), 1.34–1.23 (m, 6H).

(R)-(+)-5-[1-(2-ISOPROPYLIMIDAZOL)METHYL]-4,5-DIHYDRO-3,3-DIPHENYL-2(3H)FURANONE HYDROCHLORIDE

To a solution of 2.05 g (5.7 mmol.) of R)-(+)-5-[1-(2isopropylimidazol)methyl]-4,5-dihydro-3,3-diphenyl-2(3H)furanone in 200 mL of ethyl acetate was added 5.7 mL (5.7 mmol.) of a 1 N solution of hydrogen chloride in ether. The crystalline solid (1.92 g, 85%) was filtered, mp 233°–234° C.). Optical rotation for 0.0150 g diluted to 2.0 mL with 95% ethanol at 21° C.: [α]D+20.27°. IR (KBr) 3435, 2499, 1767, 1600, 1180, 753, 700 cm$^{-1}$. $^1$H NMR (CDCl$_3$)δ 7.43 (d, J=1.6 Hz, 1H), 7.37–7.20 (m, 11H), 4.73–4.62 (m, 2H), 4.38–4.28 (m, 1H), 3.41–3.33 (m, 2H), 2.72–7.68 (m, 1H), 1.58–1.47 (m, 6H). Anal. calcd. for C$_{23}$H$_{24}$N$_2$O$_2$+HCl: C, 69.60; H, 6.35; N, 7.06; Cl, 8.93. Found: C, 69.40; H, 6.31; N, 6.85; Cl, 8.72.

(S)-(−)-5-[1-(2-Isopropylimidazol)methyl]-4,5-dihydro-3,3-diphenyl-2(3H)furanone hydrochloride was obtained from (S)-glycerol acetonide via an analogous sequence.

EXAMPLE XV

2,2-DIPHENYL-4-METHYL-4-PENTENOIC ACID

A solution of diphenylacetic acid (14 g, 66 mmol.) in 150 mL of tetrahydrofuran was stirred at 0° C. under argon while 55.5 mL of a 2.5 M solution of n-butyllithium in hexane was added dropwise. After 15 minutes, 3-chloro-2-methylpropene (6.51 mL, 66 mmol.) was added in one portion. After 10 minutes, 25 mL of 4N hydrochloric acid was added, along with ether (250 mL). The layers were separated, the organic layer was washed with water (2×100 mL), brine (2×100 mL) dried (MgSO$_4$), and filtered. Concentration afforded 20.2 g (99%) of a yellow oil. $^1$H NMR (CDCl$_3$)δ 7.4–7.2 (m, 10H), 4.7 (s, lH), 4.6 (s, lH), 3.2 (s, 2H), 1.4 (s, 3H).

5-(BROMOMETHYL)-4,5-DIHYDRO-3,3-DIPHENYL-5-METHYL-2(3H)FURANONE

To a stirred mixture of tetrahydrofuran:water (5:1, 100 mL) was added 2,2-diphenyl-4-methyl-4-pentenoic acid (19.5 g, 73 mmol.) and sodium bicarbonate (6.15 g, 73 mmol.). After 30 minutes, bromine (3.7 mL, 73 mmol.) was added dropwise. After stirring 40 minutes, a solution of sodium thiosulfate (3 g) in 50 mL of water was added. Ether (100 mL) was added and the layers separated. The organic layer was washed with brine, dried (MgSO$_4$) and filtered. Concentration afforded a yellow solid. Recrystallization from ethyl acetate afforded 15 g (60%) of a white solid, mp 146°–148° C. IR (KBr) 1766 cm$^{-1}$. $^1$H NMR (CDCl$_3$)δ 7.4–7.2 (m, 10H), 3.4 (m, 3H), 2.9 (d, lH), 1.5 (s, 3H).

5-[1-(2-METHYLIMIDAZOL)METHYL]-4,5-DIHYDRO-3,3-DIPHENYL-5-METHYL-2(3H)FURANONE 5-(Bromomethyl)-4,5-dihydro-3,3-diphenyl-5-methyl-2(3H)furanone (3.0 g, 8.7 mmol.), 2-methylimidazole (1.5 g, 18 mmol.) and dimethylformamide (6 mL) were placed in a sealed tube. The tube was filled with argon, capped and heated at 150° C. for 65 hours. After the solution was cooled, the mixture was partitioned between saturated sodium bicarbonate solution (20 mL) and methylene chloride (100 mL) and the layers separated. The organic layer was washed with water (2×50 mL), then washed with brine and dried (MgSO$_4$). Filtration, followed by concentration, afforded a solid. Recrystallization from ethyl acetate-hexane gave 1.70 g (57%) of a white, crystalline solid, mp 166°-167° C. IR (KBr) 1758 cm$^{-1}$. $^1$H NMR (CDCl$_3$)δ 7.05-6.55 (m, 12H), 3.59 (AB q, J=15.12 Hz, 2H), 2.59 (AB q, J=13.68 Hz, 2H), 2.01 (s, 3H), 0.84 (s, 3H). Anal. calcd. for C$_{22}$H$_{22}$N$_2$O$_2$0.25 H$_2$O: C. 75.28; H, 6.47; N, 7.97. Found: C, 75.30; H, 6.50; N, 7.52.

EXAMPLE XVI

5-METHYL-3,3-DIPHENYL-2(3H)FURANONE AND 5-METHYLENE-4,5-DIHYDRO-3,3-DIPHENYL-2(3H)FURANONE

A stirred solution 22 g (66 mmol.) of 5-bromomethyl4,5-dihydro-3,3-diphenyl-2(3H)furanone and 10.47 mL (70 mmol.) of 1,8-diazabicyclo[5.4.0]undec-7-ene (DBU) in 65 mL of benzene was heated at reflux under argon for 20 hours. The resulting mixture was cooled to 25° C. and filtered. To the filtrate was added 150 mL of 10% hydrochloric acid and 200 mL of ether. The organic layer was separated and washed successively with 2N hydrochloric acid, water, a saturated aqueous solution of sodium bicarbonate and water. After being dried over sodium sulfate, the solution was concentrated to give 16.12 g (97%) of a crude liquid. TLC (silica, ethyl acetate) R$f$ 0.64. $^1$H NMR (CDCl$_3$) 7.34-7.08 (m), 5.69 (br s, 1H), 4.78 (s), 4.41 (m), 3.64 (d), 3.54 (s), 2.08 (s), 2.02 (s). Integration of the NMR spectrum and comparison of the ratios of the resonances at 5.69 (vinyl H) and 4.78 (methylene H) showed a product ratio of 70:30 for the unsaturated methyl lactone to the methylene lactone.

5-BROMOMETHYL-3,3-DIPHENYL-2(3H)FURANONE AND 4-BROMO-5-METHYLENE-4,5-DIHYDRO-3,3-DIPHENYL-2(3H)FURANONE

A stirred mixture of 4.30 g (1.7 mmol.) of the crude mixture of 5-methyl-3,3-diphenyl-2(3H)furanone and 5-methylene-4,5-dihydro-3,3-diphenyl-2(3H)furanone, 4.62 g (2.6 mmol.) of N-bromosuccinimide and 0.05 g of 2,2$^1$-azobis(2-methylpropionitrile) in 40 mL of carbon tetrachloride was stirred and refluxed under argon for 20 hours. After being cooled to 25° C., the mixture was poured into 200 mL of water and extracted with ether. The ether extracts were washed with water, dried over sodium sulfate and concentrated to give 6.57 g of a crude liquid. $^1$H NMR (CDCl$_3$) 7.4-7.05 (m), 6.26(s), 6.25 (2), 6.09 (s), 5.9 (s), 4.5-4.2 (m), 4.13 (s), 3.62 (d), 2.77 (s), 2.05 (s), 1.72 (2), 1.5 (br m). Examination of the integration of the NMR spectrum revealed a 60:40 ratio of the bromomethyl product and a secondary bromomethylene lactone.

5-[1-(2-ISOPROPYLIMIDAZOL)METHYL]-3,3-FURANONE HYDROCHLORIDE HYDRATE

A mixture of 6.5 g (19 mmol.) of a crude mixture (60:40) of 5-bromomethyl-3,3-diphenyl-2(3H)furanone and 4-bromo-5-methylene-4,5-dihydro-3,3-diphenyl-2(3H)furanone, 3.25 g (29 mmol.) of 2-isopropylimidazole and 1.0 g (9 mmol.) of sodium carbonate in 25 mL of dimethylformamide under argon in a sealed tube was heated at 115° C. for 7 hours and at 80° C. for 20 hours. The mixture was then stirred at 25° C. for 2 days. The mixture was poured into saturated aqueous sodium bicarbonate (75 mL) and extracted with ether. The combined organic layers were washed with saturated sodium bicarbonate, water, and dried over sodium sulfate. Filtration and removal of solvent gave 4.95 g of a dark frothy semi-solid. TLC (silica, ethyl acetate) R$f$ 0.1. R$f$ 0.26, R$f$ 0.35, R$f$ 0.8 with the desired lactone imidazole at R$f$ 0.26.° Column chromatography on Merck (230-400 mesh) silica gel with elution gradient from 9:1 hexane : ethyl acetate to 100% ethyl acetate afforded 0.88 g (13%) of the free base as a sticky brown residue. $^1$H NMR (CDCl$_3$) 7.33-7.20 (m, 10H), 7.02 (d, 1H), 6.89 (d, 1H), 5.71 (t, J=1.5, 1H), 4.83 (d, 2H), 3.02-2.97 (m, 1H), 1.79 (s), 1.35-1.21 (m, 6H).

The free base (0.85 g, 2.3 mmol.) was dissolved in 10 mL of hot methanol and diluted with 50 mL of ether. To the warm mixture was added 2.3 mL (2.3 mmol.) of 1N hydrogen chloride in ether. The mixture was allowed to cool and then placed in the freezer overnight. The solids were filtered and washed with ether. The tan solids were dried under vacuum at 100° C. to afford 0.700 g (1.7 mmol.) of the hydrochloride, mp 209°-211.5° C. Solubility [>1 mg/mL in 0.5N HCl and 1 drop of Tween 80 ]. $^1$H NMR (DMSO-d$_6$) 7.69 (d, 2H), 7.39-7.21 (m, 10H), 6.64 (s, 1H), 5.41 (s, 2H), 3.56-3.44 (m, 1H), 3.36 (br s, H$_2$O), 1.26 (d, 6H). IR (KBr) 3412, 3055, 2980, 2936, 2697, 1797, 1600, 1509, 1494, 1448, 1134, 1085, 949, 763, 699 cm$^{-1}$. Anal. calcd. for C$_{23}$H$_{22}$N$_2$O$_2$. HCl . 0.75 H$_2$O: C, 69.95; H, 5.87; N, 7.09; Cl, 8.98. Found: C, 67.66, 67.60; H, 6.02, 6.04; N, 6.91; Cl, 8.70. TLC (silica, ethyl acetate) R$f$ 0.40.

5-[1-(2-Ethylimidazol)methyl]-3,3-diphenyl-2(3H)furanone was prepared from 2-ethylimidazole and the bromolactone mixture in an analogous fashion. The base was a tan solid, mp 102°-103° C. after trituration with ether $^1$H NMR (CDCl$_3$) 7.4-7.2 (m, 10H), 7.01 (d, 1H), 6.95 (d, 1H), 5.7 (s, 1H), 4.8 (s, 2H), 2.6 (q, 2H), 1.4 (t, 3H). IR (KBr) 2975, 1794, 1687 cm$^{-1}$. Anal. calcd. for C$_{22}$H$_{20}$N$_2$O$_2$: C, 76.72; H, 5.85; N, 8.13. Found: C, 76.47; H, 5.89; N, 8.09.

EXAMPLE XVII

5-[1-(3-METHYL-2-N-PROPYL)IMIDAZOL]-METHYL-4,5-DIHYDRO-3,3-DIPHENYL-2(3H)FURANONE IODIDE

A mixture of 2.75 g (7.6 mmol.) of 5-[1-(2-n-propyl)imidazol]methyl-4,5-dihydro-3,3-diphenyl-2(3H)furanone and 10 mL of iodomethane was heated in a sealed tube for 20 minutes at 120° C. After being cooled to 25° C., excess iodomethane was evaporated under a stream of nitrogen. Trituration of the residual solid with acetone afforded 3.5 g (92%) of the quaternary salt, mp 207°-210° C. $^1$H NMR (CDCl$_3$)δ .954 (t, J=7.2 Hz 3H) 1.52-1.68 (m 2H), 2.82-2.94 (m, 1H), 2.95-3.08 (m, 2H), 3.26-3.36 (m, 1H); 3.80 (m, 3H), 4.48-4.70 (m, 3H), 7.24–7.44 (s, 10H), 7.64–7.70 (m, 2H); IR (KBr) 3090, 3059, 2982, 2933, 1756, 1226, 1175, 1154, 707, 696 cm$^{-1}$; analytical TLC (silica, 95:5, methylene chloride: MeOH) R$f$ .15. Anal. calcd. for $C_{24}H_{27}IN_2O_2$: C, 57.38 H, 5.41; I, 25.25; N, 5.57. Found: C, 57.46; H, 5.43; I, 25.16; N, 5.56.

The following quaternary salts were prepared in an analogous manner.

5-[1-(2-Isopropyl-3-methylimidazol)methyl]-4,5-dihydro-3,3-diphenyl-2(3H)furanone Iodide Hydrate (mp 216°–217° C.)

5-[1-(2-Ethyl-3-methylimidazol)methyl]-4,5-dihydro-3,3-diphenyl-2(3H)furanone Iodide Hydrate (mp 219.5°–221° C.), 5-[1-(2-tert-Butyl-3-methylimidazol)methyl]-4,5-dihydro-3,3 -diphenyl-2(3H)furanone Iodide Hydrate (mp 213°–214.5° C.), 5-[1-[2-(2-Methoxyethyl)-3-methylimidazol]methyl]-4,5-dihydro-3,3-diphenyl-2(3H)furanone Iodide Hydrate (mp 179°–183° C.).

EXAMPLE XVIII

ANTIMUSCARINIC TEST PROTOCOL

This protocol was designed to identify compounds that possess antagonist activity at postsynaptic muscarinic cholinergic receptors on intestinal (ileal-longitudinal) smooth muscle and bladder detrusor muscle.

PREPARATION OF ILEUM FOR TESTING

Male albino guinea pigs are killed by decapitation or cervical dislocation. The cavity is opened and the small intestine is removed, with about 10 cm of the terminal ileum being discarded. The intestine is placed in a Petri dish that contains Tyrodes solution (137 mM NaCl, 2.7 mM KCl, 1.8 mM $CaCl_2 \cdot 2H_2O$, 1.1 mM $MgCl_2 \cdot 6H_2O$, 0.4 mM $NaH_3PO_4$, 11.8 mM $NaHCO_3$, 5.6 mM dextrose) and cut into 3–4 cm segments. The segments are preferentially taken from the aboral end of the ileum. Each segment is carefully stretched onto a glass rod 6 mm in diameter and the remaining mesenteric tissue is cut away. The longitudinal muscle, with the myenteric plexus attached, is separated from the underlying circular muscle by gently stroking with a cotton-tipped applicator soaked in Tyrodes solution on a tangent away from the shallow longitudinal incisions made parallel to the mesenteric attachment. Using gentle traction, and taking care to keep the segment moist throughout the whole procedure, the tissue is stripped from the whole length of the segment (Paton and Zar, *J. Physiol.* 194:13, 1968).

Tissues are suspended with 5-0 silk suture in 10 mL water-jacketed glass tissue baths containing Tyrodes solution maintained at 37° C. and aerated with 95% $O_2$/5% $CO_2$. The suture connects each tissue to an isometric force-displacement transducer (Grass or Gould) coupled to a physiograph. Each preparation is suspended under a resting tension of 0.3 g and allowed to equilibrate for 36 minutes. During this period, the baths are emptied and filled every 12 minutes with 10 mL of warm Tyrodes solution. At the end of this equilibration period, each muscle strip is conditioned by adding 10 μM carbachol to the baths. The drug remains in contact with each tissue for 1–2 minutes and then is removed from the bath with 4 rapid rinses of 10 mL of warm Tyrodes solution. The preparations are allowed to recover for an additional 12 minutes before being used in experiments.

PREPARATION OF BLADDER FOR TESTING

Male albino guinea pigs are killed by decapitation or cervical dislocation. The peritoneal cavity is opened and the bladder is held lightly at its apex, stretched gently, and fat is lifted with fine forceps and dissected away in situ with blunt-tipped scissors as close to the surface of the bladder as possible. The tissue is placed in a latex-bottomed Petri dish that contains a modified Krebs solution (133 mM NaCl, 1.3 mM $NaH_3PO_4$, 16.3 mM $NaHCO_3$, 4.7 mM KCl, 0.6 mM $MgSO_4 \cdot 7H_2O$, 2.5 mM $CaCl_2 \cdot 2H_2O$, 7.7 mM dextrose) and cut above the neck. The bladder is collapsed into a flat pouch, which is opened by two lateral incisions and unfolded to give a rectangular sheet of tissue approximately 2 cm long and 1 cm wide. The sheet is gently stretched and pinned to the bottom of the Petri dish. Blunt separation of the mucosa, which is visible as a looser superficial pink layer, is started at one end by carefully inserting the blades of micro dissecting scissors between the mucosa and muscle layers and using gentle spreading of the blades, together with steady traction with forceps to tease the two layers apart. Clean removal of the mucosa is usually possible without any fraying or tearing of the underlying muscle. The removal of the mucosa is considered essential for improving oxygen supply to the preparation and for providing better access on both sides of the thin muscle sheet for administered drugs (Ambache and Zar, *J. Physiol.* 210:671, 1970). The sheet is trimmed, if necessary, and cut longitudinally into four strips.

The strips are tied off with 5-0 silk suture and are then suspended in 10 mL water-jacketed glass tissue baths containing the Krebs solution maintained at 35° C. and aerated with 95% $O_2$/5% $CO_2$. The suture connects each tissue to an isometric force-displacement transducer (Grass or Gould) coupled to a physiograph. Each preparation is suspended under a resting tension of 0.5 g and allowed to equilibrate for 36 minutes. During this period, the baths are emptied and filled every 12 minutes with 10 mL of warm Krebs buffer. At the end of this period, each muscle strip is conditioned by adding 10 μM carbachol to the baths. The drug remains in contact with each tissue for 1–2 minutes and then is removed by four rapid rinses of 10 mL of warm Krebs buffer. The preparations are allowed to recover for an additional 12 minutes before being used in experiments.

PREPARATION OF AGONIST

Carbachol is dissolved in saline to produce $2 \times 10^{-2}$ M stock concentrations. Serial dilutions (1:10) in saline or water are made from the stock solution. Appropriate volumes of these solutions are added cumulatively to the 10 mL tissue baths in order to obtain the desired bath concentrations.

PREPARATION OF TEST COMPOUNDS

Compounds that are soluble in water or saline are dissolved in these solvents to produce $2 \times 10^{-2}$ or $2 \times 10^{-3}$ M stock concentrations. Small amounts of 1N HCl, NaOH, or 95% ethanol may be added for those agents that are not soluble in water or saline alone. Serial dilutions (1:10) in saline or water are made from the stock solution. Compounds that are insoluble in aqueous solvents are dissolved in dimethylsulfoxide (DMSO) to produce $4 \times 10^{-2}$ M stock solutions. Serial dilutions (1:10) in water are made from the stock solution. Other solvents may be used when appropriate and will be specifically described in the experimental procedure. Appropriate volumes are then added to the baths in order to obtain the desired bath concentrations.

EXPERIMENTAL PROCEDURE

Appropriate volumes of carbachol solutions are cumulatively added to the 10 mL tissue baths to increase the concentration of carbachol in the bath step-by-step without washing out after each single dose. With each concentration step, the tissue contracts isometrically. The next concentration is added only after the preceding contraction has reached a steady value. When the next concentration step does not cause a further decrease in contraction, it is assumed that the maximum effect has been obtained. The tissue is then washed with 4 rapid rinses of 10 mL of warm Tyrodes solution and allowed to recover for 12 minutes [Van Rossum et al.. *Arch. Int. Pharmacodyn.* 143:240, (1963) and 143:299, (1963)]. Antagonism of carbachol responses in the presence of antagonist are determined by repeating the cumulative addition procedure after the tissue has been exposed to the agonist for 5 minutes.

Three of four different concentrations of antagonist are studied in the same preparations. Responses are expressed relative to the maximum contraction elicited by carbachol in the absence of antagonist. The data are collected via Buxco Data Logger and analyzed by Branch Technology's software package to obtain Kb values for the antagonists.

EXAMPLE XIX

PRIMARY IN VIVO BRONCHODILATOR ASSAY FOR MUSCARINIC ANTAGONISTS

Male Guinea pigs were anesthetized by urethane. The trachea, carotid artery and jugular vein were cannulated. Animals were ventilated with room air at a constant rate and volume. Airway pressure was measured from a side port of the tracheal catheter, and blood pressure and heart rate were monitored as well.

After a stable baseline period, an aerosol of carbachol was administered via an ultrasonic nebulizer. Once the bronchoconstrictor response plateaued, test compound was given in increasing i.v. doses to cause graded, cumulative reductions in airway pressure. If more than a 50% reversal of bronchoconstriction occurred, an $ED_{50}$ value for bronchodilator potency was calculated using a probit analysis. The $ED_{50}$ was defined as the cumulative i.v. dose that caused a 50% reversal of bronchoconstriction.

| Compound | Muscarinic Antagonist Activity | | Bronchodilator Activity |
|---|---|---|---|
| | Ileum Kb, nM | Bladder Kb, nM | $ED_{50}$, mg/kg, i.v. |
| 5-[(1-Imidazol)methyl]-4,5-dihydro-3,3-diphenyl-2(3H)furanone | 373 | — | — |
| 5-[1-(2-Methylimidazol)methyl]-4,5-dihydro-3,3-diphenyl-2(3H)furanone | 107 | 238 | 5.5 |
| 5-[1-(2-Ethylimidazol)methyl]-4,5-dihydro-3,3-diphenyl-2(3H)furanone hydrochloride | 68 | 86 | 4.0 |
| 5-[1-(3-Methylimidazol)methyl]-4,5-dihydro-3,3-diphenyl-2(3H)furanone bromide hydrate | 322 | 151 | 1.0 |
| 5-[1-(2,3-Dimethylimidazol)methyl]-4,5-dihydro-3,3-diphenyl-2(3H)furanone bromide | 71 | — | 0.85 |
| 5-[1-(2-Isopropylimidazol)methyl]-4,5-dihydro-3,3-diphenyl-2(3H)-furanone hydrochloride | 30 | 33 | 0.83 |
| 5-[1-(2-n-Propylimidazol)methyl]-4,5-dihydro-3,3-diphenyl-2(3H)-furanone hydrochloride | 21 | 70 | 1.3 |
| 5-[1-(2-Methyl-3-benzylimidazol)methyl]-4,5-dihydro-3,3-diphenyl-2(3H)furanone bromide | 544 | — | — |
| 5-[1-(2-n-Butylimidazol)methyl]-4,5-dihydro-3,3-diphenyl-2(3H)furanone | 113 | — | >10 |
| 5-[(1-Benzimidazol)methyl]-4,5-dihydro-3,3-diphenyl-2(3H)furanone | 1281 | — | — |
| 5-[1-(Ethylimidazol)methyl]-4,5-dihydro-3,3-diphenyl-2(3H)furanone bromide | 229 | — | — |
| 5-[1-(2-Ethylimidazol)methyl]-3,3-diphenyl-2(3H)furanone | 8.2 | — | 1.9 |
| 5-[1-(2-Ethyl-4-methylimidazol-methyl]-4,5-dihydro-3,3-diphenyl-2(3H)furanone hydrobromide | 86 | — | — |
| 5-[1-(3-Methyl-2-n-propylimidazol-methyl]-4,5-dihydro-3,3-diphenyl-2(3H)furanone iodide | 23 | 11 | 0.11 |
| 5-[1-(3-Methylimidazol)methyl]-4,5-dihydro-5-methyl-3,3-diphenyl-2(3H)furanone hydrate | 370 | 317 | — |
| 5-[1-(2-Isopropyl-3-methylimidazol-methyl]-4,5-dihydro-3,3-diphenyl-2(3H)furanone bromide | 2.9 | 0.7 | 0.007 |

-continued

| Compound | Muscarinic Antagonist Activity | | Bronchodilator Activity |
|---|---|---|---|
| | Ileum Kb, nM | Bladder Kb, nM | ED$_{50}$, mg/kg, i.v. |
| 5-[1-(2-Ethyl-3-methylimidazol)methyl]-4,5-dihydro-3,3-diphenyl-2(3H)furanone bromide | 8 | 5 | 0.13 |
| (S)-(−)-5-[1-(2-Ethylimidazol)methyl]-4,5-dihydro-3,3-diphenyl-2(3H)furanone hydrochloride | 169 | 350 | — |
| (R)-(+)-5-[1-(2-Ethylimidazol)methyl]-4,5-dihydro-3,3-diphenyl-2(3H)furanone hydrochloride | 21 | 129 | — |
| 5-[1-(2-Isobutylimidazol)methyl]-4,5-dihydro-3,3-diphenyl-2(3H)-furanone hydrochloride | 489 | — | >10 |
| 5-[1-(2-tert-Butylimidazol)methyl]-4,5-dihydro-3,3-diphenyl-2(3H)furanone hydrochloride | 3.3 | — | 0.14 |
| 5-[1-(4-Phenylimidazol)methyl]-4,5-dihydro-3,3-diphenyl-2(3H)-furanone hydrochloride hydrate | 140 | — | Insol. |
| 5-[1-(2-Phenylimidazol)methyl]-4,5-dihydro-3,3-diphenyl-2(3H)-furanone | 5920 | — | >6 |
| 5-[1-[2-(2-Methoxymethyl)-imidazol]methyl]-4,5-dihydro-3,3-diphenyl-2(3H)furanone hydrochloride hydrate | 67 | — | >10 |
| 6,7-Dihydro-1-[(2,3,4,5-tetrahydro-5-oxo-4,4-diphenyl-2-furanyl)methyl]-5H-pyrrolo[1,2-a]imidazolium chloride hydrate | 33 | — | 0.7 |
| 5-[1-(2-Ethoxymethylimidazol)methyl]-4,5-dihydro-3,3-diphenyl-2(3H)furanone | >1000 | — | >10 |
| 5-[(1,8-Diazabicyclo[5.4.0]undec-7-en-8-yl)methyl]-4,5-dihydro-3,3-diphenyl-2(3H)furanone chloride hydrate | >1000 | — | >10 |
| 5-[1-(2-Isopropyl-3-methylimidazol)methyl]-4,5-dihydro-3,3-diphenyl-2(3H)furanone iodide | 4 | 2.4 | 0.06 |
| 5-[1-(Ethoxymethyl-3-methylimidazol)methyl]-4,5-dihydro-3,3-diphenyl-2(3H)furanone iodide | 253 | 339 | >10 |
| 5-[1-(2-Isopropylimidazol)methyl]-3,3-diphenyl-2(3H)furanone hydrochloride hydrate | 31 | — | — |
| 5-[1-(2-Methoxyethylimidazol)methyl]-4,5-dihydro-3,3-diphenyl-2(3H)furanone hydrochloride | 638 | — | >10 |
| 5-[1-(2-Methoxymethyl-3-methylimidazol)methyl]-4,5-dihydro-3,3-diphenyl-2(3H)furanone iodide | 40 | — | — |
| 5-[1-(2-Methoxyethyl-3-methylimidazol)methyl]-4,5-dihydro-3,3-diphenyl-2(3H)furanone iodide hydrate | 39 | — | — |
| 5-[1-(2-Carbomethoxyimidazol)methyl]-4,5-dihydro-3,3-diphenyl-2(3H)furanone hydrochloride | 435 | — | — |
| 1-[(2,3,4,5-Tetrahydro-5-oxo-4,4-diphenyl-2-furanyl)methyl]imidazo[1,2-a]pyridinium chloride hydrate | 45 | — | — |
| (R)-(+)-5-[1-(2-Isopropylimidazol)methyl]-4,5-dihydro-3,3-diphenyl-2(3H)furanone hydrochloride | 10 | 15 | — |
| 1-[(2,3,4,5-Tetrahydro-5-oxo-4,4-diphenyl-2-furanyl)methyl]-8-methylimidazo[1,2-a]pyridinium chloride hydrate | 74 | — | — |
| 5-[1-(2-Benzylimidazol)methyl]-4,5-dihydro-3,3-diphenyl-2(3H)-furanone hydrochloride | 223 | — | — |
| 5,6,7,8-Tetrahydro-1-[(2,3,4,5-tetrahydro-5-oxo-4,4-diphenyl-2-furanyl)methyl]imidazo[1,2-a]- | — | — | — |

-continued

| | Muscarinic Antagonist Activity | | Bronchodilator Activity |
|---|---|---|---|
| Compound | Ileum Kb, nM | Bladder Kb, nM | ED$_{50}$, mg/kg, i.v. |
| pyridinium chloride hydrate | | | |

What is claimed is:

1. A compound of the formula:

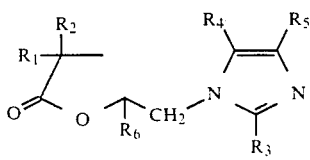

or a pharmaceutically acceptable salt thereof wherein:
the dashed line indicates either the 4,5-unsaturated or the 4,5-dihydrofuranone ring;
$R_1$ and $R_2$ are independently selected from the group consisting of hydrogen, thienyl, furanyl, cycloalkyl ($C_3$–$C_6$), benzyl, phenyl and substituted benzyl and substituted phenyl, wherein the phenyl or benzyl substituents are selected from halogen, trifluoromethyl, hydroxy, lower alkoxy and lower alkyl;
$R_3$, $R_4$ and $R_5$, which may be the same or different, are selected from the group consisting of hydrogen, halogen, trifluoromethyl, nitro, lower alkyl, lower alkyl substituted with a halogen, lower alkoxy, amino or carboxylic acid group, an alkylene bridge between $R_4$ and $R_5$ or $R_3$ and the ring N, a cycloalkyl group containing 3 to 6 carbons, benzyl, phenyl, substituted benzyl and substituted phenyl wherein the benzyl and phenyl substituents are selected from halogen, trifluoromethyl, hydroxy, lower alkoxy and lower alkyl.
$R_6$ in the dihydrofuranone series is hydrogen or lower alkyl.

2. The compound of claim 1 wherein $R_1$ and $R_2$ are independently selected from phenyl, thienyl, furanyl, substituted phenyl, and $R_3$, $R_4$ and $R_5$ are each independently a lower alkyl.

3. The compound of claim 1 wherein $R_1$ and $R_2$ are phenyl and $R_3$, $R_4$ and $R_5$ are each independently a lower alkyl.

4. The compound of claim 1 wherein $R_1$ and $R_2$ are phenyl, and $R_3$ is a lower alkyl and $R_4$ and $R_5$ are hydrogen.

5. The compound of claim 1 which is 5-[1-(2-ethylimidazol)methyl]-4,5-dihydro-3,3-diphenyl-2(3H)furanone.

6. The compound of claim 1 which is (R)-(+)-5-[1-(2-ethylimidazol)methyl]-4,5-dihydro-3,3-diphenyl-2(3H)furanone.

7. The compound of claim 1 which is 5-[1-(2propylimidazol)methyl]-4,5-dihydro-3,3-diphenyl-2(3H)furanone.

8. The compound of claim 1 which is 5-[1-(2methylimidazol)methyl]-4,5-dihydro-3,3-diphenyl-2(3H)furanone.

9. The compound of claim 1 which is 5-[1-(2-n-propylimidazol)methyl]-4,5-dihydro-3,3-diphenyl-2(3H)furanone.

10. The compound of claim 1 which is 5-[1-(2ethylimidazol)methyl]-3,3-diphenyl-2(3H)furanone.

11. The compound of claim 1 which is 5-[1-(2-ethyl-3-methylimidazol)methyl]-4,5-dihydro-3,3-diphenyl-2(3H)furanone bromide.

12. The compound of claim 1 which is 5-[1-(2-tert-butylimidazol)methyl]-4,5-dihydro-3,3=diphenyl-2(3H)furanone.

13. The compound of claim 1 which is 6,7-dihydro-1-[(2,3,4,5-tetrahydro-5-oxo-4,4-diphenyl-2furanyl)methyl]-5H-pyrrolo[1,2-a]imidazolium chloride.

14. The compound of claim 1 which is 5-[1-(2isopropylimidazol)methyl]-3,3-diphenyl-2(3H)furanone.

15. The compound of claim 1 which is (R)-(+)-5-[1-(2isopropylimidazol)methyl]-4,5-dihydro-3,3-diphenyl-2(3H)furanone.

16. The compound of claim 1 which is 5-[1-(2isopropylimidazol)methyl]dihydro-3,3-diphenyl-2(3H)furanone.

17. A pharmaceutical composition for use as a cholinergic receptor antagonist comprising an effective amount of the compound of claim 1 and a pharmaceutically acceptable carrier.

18. A pharmaceutical composition for treatment of neurogenic bladder disorder comprising an effective amount of the compound of claim 1 and a pharmaceutically acceptable carrier.

19. A pharmaceutical composition for use as an antispasmodic agent comprising an effective amount of the compound of claim 1 and a pharmaceutically acceptable carrier.

20. A pharmaceutical composition for use as an antisecretory agent comprising an effective amount of the compound of claim 1 and a pharmaceutically acceptable carrier.

21. A pharmaceutical composition for use as a mydriatic agent comprising an effective amount of the compound of claim 1 and a pharmaceutically acceptable carrier.

22. A method for treating a disorder responsive to an anticholinergic agent comprising administering to a patient an effective amount of a compound of claim 1.

23. A method for treating neurogenic bladder disorder comprising administering to a patient an effective amount of a compound of claim 1.

24. A method for treating irritable bowel syndrome comprising administering to a patient an effective amount of a compound of claim 1.

25. A method for treating spastic colitis comprising administering to a patient an effective amount of a compound of claim 1.

26. A method for treating ulcerative colitis comprising administering to a patient an effective amount of a compound of claim 1.

27. A method for treating diverticulitis comprising administering to a patient an effective amount of a compound of claim 1.

28. A method for treating diarrhea comprising administering to a patient an effective amount of a compound of claim 1.

29. A method for treating hypertension comprising administering to a patient an effective amount of a compound of claim 1.

30. A method for treating chronic obstructive pulmonary diseases comprising administering to a patient an effective amount of a compound of claim 1.

* * * * *

UNITED STATES PATENT AND TRADEMARK OFFICE
CERTIFICATE OF CORRECTION

PATENT NO. : 5,039,691

DATED : Aug. 13, 1991

INVENTOR(S) : Spagnuolo et al.

It is certified that error appears in the above-identified patent and that said Letters Patent is hereby corrected as shown below:

The formula in the Abstract, at column 2 lines 1 to 8 and in Claim 1 should be as follows:

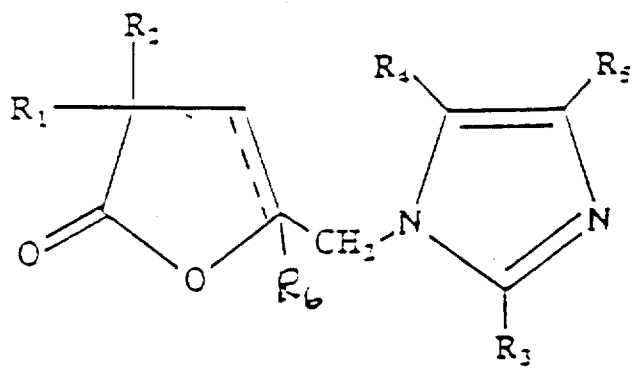

Signed and Sealed this

First Day of February, 1994

Attest:

BRUCE LEHMAN

Attesting Officer

Commissioner of Patents and Trademarks